United States Patent [19]

May

[11] 4,302,856
[45] Dec. 1, 1981

[54] ARTIFICIAL LIMBS
[75] Inventor: Denis R. W. May, London, England
[73] Assignee: J. E. Hanger & Company Limited, London, England
[21] Appl. No.: 56,162
[22] Filed: Jul. 10, 1979
[30] Foreign Application Priority Data
  Aug. 3, 1978 [GB] United Kingdom ............... 32146/78
[51] Int. Cl.³ ........................... A61F 1/04; A61F 1/08
[52] U.S. Cl. ................................................. 3/30; 3/6; 3/7; 3/21
[58] Field of Search ....................... 3/7, 30, 33, 31, 32, 3/6, 21
[56] References Cited
U.S. PATENT DOCUMENTS

| 53,931 | 4/1866 | Weston et al. | 3/31 X |
| 710,996 | 10/1902 | Peer | 3/31 X |
| 1,090,881 | 3/1914 | Rowley | 3/7 X |
| 2,289,154 | 7/1942 | Von Cise | 3/32 |
| 2,390,920 | 12/1945 | Caron | 3/32 |
| 2,439,195 | 4/1948 | Witmyer et al. | 3/31 UX |
| 2,594,752 | 4/1952 | Fahlstrom | 3/30 |
| 3,671,978 | 6/1972 | May | 3/21 X |
| 3,940,804 | 3/1976 | Benton et al. | 3/30 |

FOREIGN PATENT DOCUMENTS 1371996 10/1974 United Kingdom ....................... 3/7

*Primary Examiner*—Barry Richman
*Attorney, Agent, or Firm*—Pollock, Vande Sande & Priddy

[57] ABSTRACT

The angular relation of a Sach foot to a shin may be adjusted during assembly to provide a desired heel height so that one type of Sach foot may be stocked for each shoe size and adapted for different heights of heel. The connecting bolt passes through a rotatable trunnion transverse to the length of the foot and is pivotable between fore and aft limits, and material is removed from the confronting surfaces of the foot and shin during fitting or packing material is inserted between them to effect such angular displacement.

4 Claims, 4 Drawing Figures

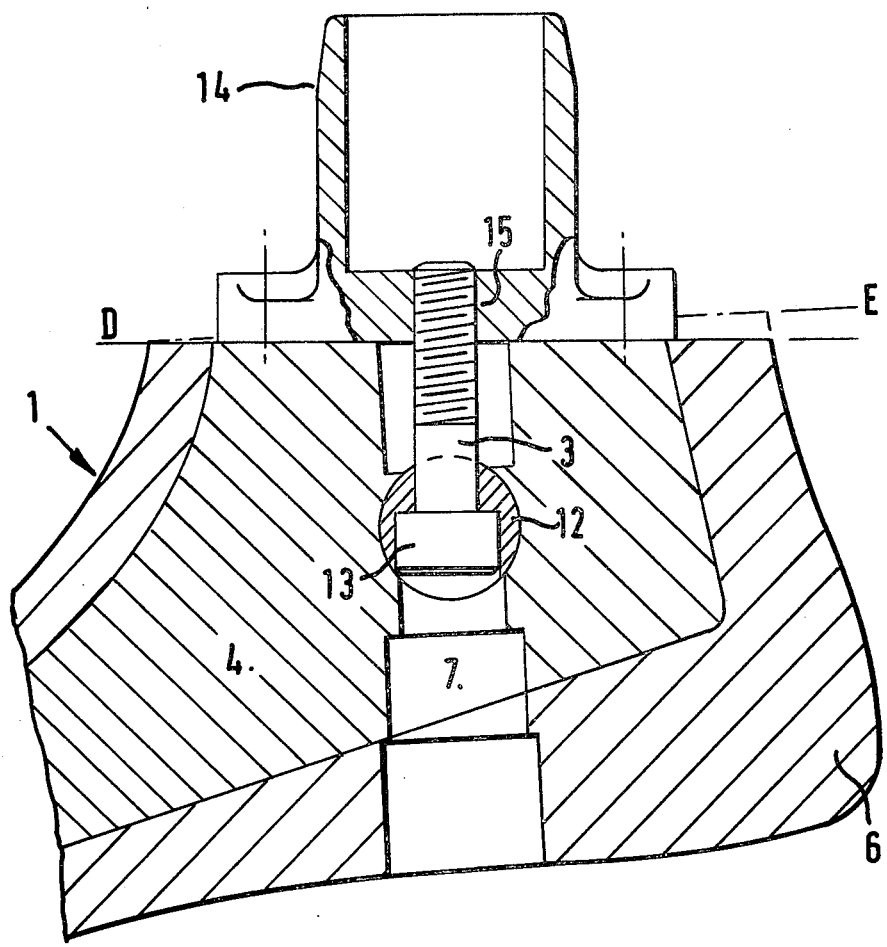

ARTIFICIAL LIMBS

FIELD OF THE INVENTION

This invention is concerned with artificial legs and particularly with the attachment of artificial feet to an artificial leg.

BACKGROUND OF THE INVENTION

The solid ankle cushion heel (Sach) foot has, for many years, been well known in the art as a simple light weight terminal device, easily fitted to the limb and stocked in standard shoe sizes. These feet are attached to the limb by a bolt passing through the foot and threaded into a nut in the limb or an internally threaded part of the limb.

The Sach foot plays an important role in limb prescription, particularly for below knee amputation. Its main disadvantage is that it comes in standard shoe sizes but is not easily adjustable for particular heel heights. With the advent of fashion shoes, not only for ladies but for men also, in all the shoe sizes, the problem of stocking in terms of heel heights for each size would be enormous and economically would limit the prescription of the foot.

SUMMARY OF THE INVENTION

An object of this invention is to provide means for attaching a foot to a limb which allows the ready adaptation of a standard foot, or of the limb to which it is attached, to different heel heights.

From one aspect, the invention provides a foot in which the bolt by which it is attached to the limb passes through a trunnion transverse to the length of the foot, whereby the angular relation of the foot to a limb may be varied at the time of assembly of the foot and limb to vary the height of the heel in use while maintaining the axis of the bolt substantially parallel to the length of the limb. Such variation of heel height may be effected by removing material from the upper surface of the solid ankle foot or the lower surface of the limb, which surfaces as taken from stock are normally perpendicular to the bolt, or by inserting wedge shaped packing between the two surfaces.

From another aspect the invention provides an artificial leg comprising a shin portion, a foot portion having a trunnion mounted transversely therein for rotation about an axis transverse to the direction of elongation of the foot portion, and a bolt passing through said trunnion and engaging a threaded member in said shin portion, whereby during assembly the angular relation of the foot and shin portions may be varied relative to one another to adapt a standard foot for use with shoes having a desired height of heel while the bolt and the shin portion in use are vertical.

The foot is preferably a Sach type foot. The shin portion may be a solid wooden or rigid plastic shin with an inserted nut into which the bolt is threaded, or may be a M.A.P. (Modular Assembly Prosthesis) limb with a Sach foot attachment casting.

BRIEF DESCRIPTION OF THE DRAWINGS

Other parts of the invention are embodied in the preferred forms which will now be described with reference to the accompanying drawings, in which:

FIG. 4 is a section of a Sach foot attached to a M.A.P. limb.

DESCRIPTION OF THE PREFERRED EMBODIMENT

Figure 1:
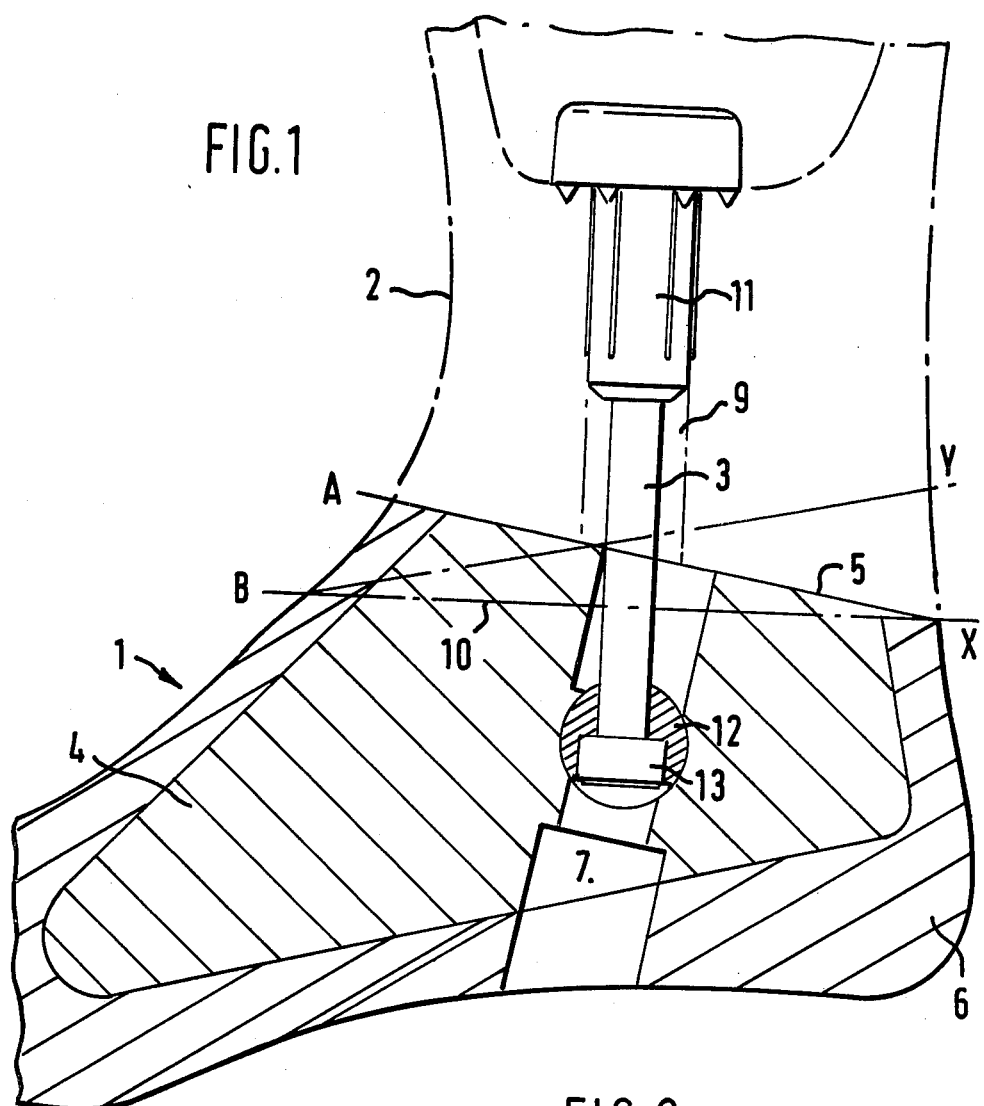
FIG. 1 is a view of a Sach foot attached to a solid shin portion so as to provide for a minimum heel height.

Referring first to FIG. 1, an artificial limb comprises a Sach foot 1 connected to a shaped shin 2 by means of a bolt 3. The foot 1 is of a standard shape for the shoe size of the intended user and comprises a keel 4 of hard wood encased except for its top surface 5 in foamed polyurethane 6. A hole 7 passes through the foot 1 with its axis at right angles to the top surface 5 when taken from stock.

The shaped shin 2 which may also be of standard shape has a hole 9 extending upwardly at right angles to its undersurface which, when taken from stock, is represented in FIG. 1 by the line 10. Hitherto the foot and the shin have been assembled by placing the surfaces 5 and 10 together and inserting a bolt through the holes 7, 9 and threading it into a nut 11 mounted in the shin 2. The heel height of a shoe that can be worn by the user is thus predetermined since it is necessary for the limb and therefor the bolt to be substantially upright when the user is standing.

Figure 2:
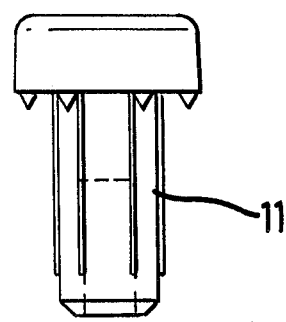
FIG. 2 is an exploded view of parts associated with the limb of FIG. 1.
Figure 2:
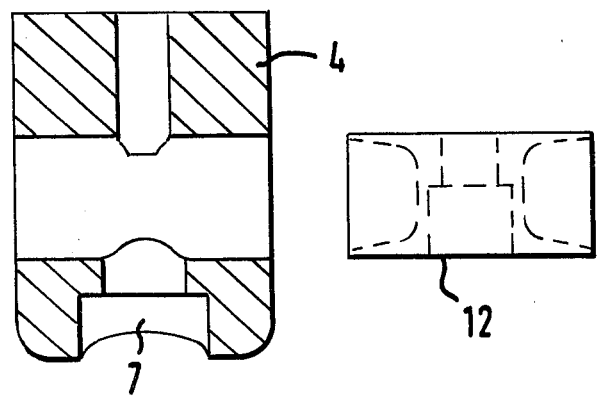
Figure 2:
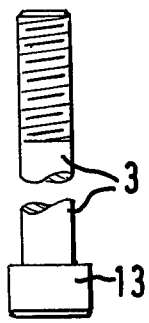

In order that, during fitting, the limb may be made to meet the user's wishes as to the heel height of the shoes he wears, a rotatable cylindrical trunnion 12 is provided in the keel 4 of the foot with its axis of rotation perpendicular to the axis of the hole 7 and the bolt 3 passes through this trunnion. The upper portion of hole 7 has a dimension substantially equal to the diameter of bolt 3 in a direction parallel to the axis of rotation of trunnion 12 as shown in FIG. 2, but is elongated in the fore-and-aft direction as shown in FIG. 1 so that the bolt 3 may pivot with the trunnion 12 between limits determined by the edges of the hole 7. The head 13 of the bolt 3 is entirely within the trunnion 12 to avoid interference with the keel when the bolt pivots.

With this arrangement, the foot 1 may be angled in relation to the shin 2 to vary the heel height at the time of assembly of the foot and shin. Either the undersurface of the shin or the top surface of the foot may be adjusted at the time of assembly to permit this. In FIG. 1, the portion indicated by A-X-B has been removed from the lower end of the shin, enabling the foot to be angled upwardly and thus provide a lower heel height than the standard. It would obviously be equally effective to remove the portion A-X-B from the top of the foot.

Figure 3:
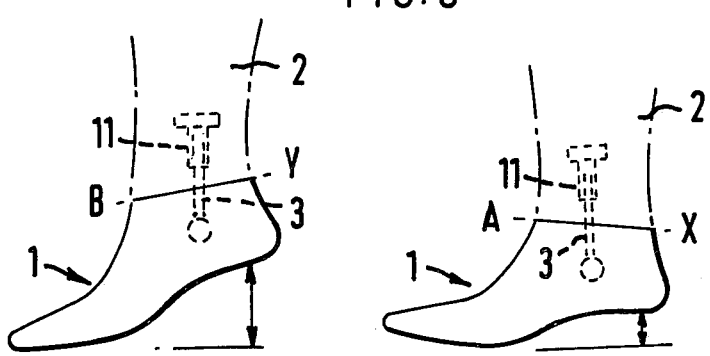
FIG. 3 shows to a smaller scale the variation in heel height that may be obtained.

If a high heel is desired, the foot is angled downwardly by removing material in the opposite sense parallel to the line BY in FIG. 1 and as shown at the left of FIG. 3.

Obviously instead of removing a wedge of material such as A-X-B from between the shin and the foot, a wedge of packing could be inserted between them with the same effect of altering the angular relationship between the shin and the foot.

FIG. 4 shows a modification in which the foot is attached to a M.A.P. limb. The limb is formed with an attachment 14 with a threaded bolt 15 into which the bolt 3 is threaded to attach the Sach foot 1. In this case, material is removed from the top of the Sach foot, for example as indicated by the line D-E, to vary the angular relation of the foot and shin as described above.

It will be seen that the invention enables one size of Sach foot to be stocked for each size of shoe and readily adapted during fitting to suit the user's requirements as to the heel height of his shoes.

It will be understood that the invention is not restricted to the details of the preferred forms described by way of example which may be modified without departure from the scope of the accompanying claims.

I claim:

1. A solid ankle artificial leg comprising an elongated shin portion, an internally threaded female member within said shin portion, the axis of said threaded female member extending parallel to the direction of elongation of said shin portion, a foot portion having a solid ankle cushioned heel, a cylindrical trunnion mounted within said foot portion for rotation about an axis which is transverse to the direction of elongation of said shin portion, a hole extending between the sole and the uppermost surface of said foot portion in intersecting relation to said cylindrical trunnion, a threaded bolt passing via the portion of said hole below said cylindrical trunnion transversely through said cylindrical trunnion and extending via the portion of said hole above said cylindrical trunnion from the interior of said foot portion to a position beyond the uppermost surface of said foot portion, said threaded bolt engaging said threaded female member within said shin portion, the head of said bolt being accessible from the sole of said foot portion via the portion of said hole below said cylindrical trunnion to screw said bolt into said female member thereby to connect said foot and shin portions together, the portion of said hole above said trunnion exhibiting a cross section which is of slot-like configuration having a width substantially equal to the diameter of said bolt and a length that is elongated in the direction of elongation of said foot portion, said bolt being pivotable through said slot-like portion of said hole, as said trunnion rotates about its axis, in the fore and aft direction of said foot portion at the time of assembly of said foot and shin portions to permit the angular relation of said foot and shin portions to be varied relative to one another at the time of assembly thereby to determine the heel height of said leg at the time of assembly, the head of said bolt being countersunk into a side wall of said cylindrical trunnion to avoid interference between said bolt head and said foot portion when said bolt and cylindrical trunnion are moved within said foot portion at the time of assembly of said foot and shin portions, the said foot and shin portions and said bolt and trunnion being fixed in position relative to one another at said determined heel height by adjusting the relation of the confronting surfaces of the shin and foot portions and by tightening said bolt into said threaded female member with said bolt extending perpendicular to the ground when the user of the artificial leg is standing.

2. A solid ankle artificial leg as defined in claim 1, wherein said foot portion comprises a standard stock foot whose uppermost surface is oriented at an angle other than that normally present in a standard stock foot to adjust the angular relation of said foot and shin portions relative to one another during assembly of said foot portion to said shin portion.

3. A solid ankle artificial leg as defined in claim 1, wherein said shin portion comprises a standard stock shin whose lowermost surface is oriented at an angle other than that normally present in a standard stock shin to adjust the angular relation of said foot and shin portions relative to one another during assembly of said foot portion to said shin portion.

4. A solid ankle artificial leg as defined in claim 1, including packing material disposed between the upper surface of said foot portion and the lower surface of said shin portion for varying the angular relation of said foot and shin portions relative to one another at the time of assembly of said foot and shin portions.

* * * * *